United States Patent
Hareland et al.

(10) Patent No.: US 11,247,056 B2
(45) Date of Patent: Feb. 15, 2022

(54) SYSTEMS AND METHODS FOR LEAD FAULT DETECTION AND RECONFIGURATION

(71) Applicant: Medtronic, Inc., Minneapolis, MN (US)

(72) Inventors: Scott A. Hareland, Lino Lakes, MN (US); Yan Liu, Maple Grove, MN (US)

(73) Assignee: Medtronic, Inc., Minneapolis, MN (US)

( * ) Notice: Subject to any disclaimer, the term of this patent is extended or adjusted under 35 U.S.C. 154(b) by 75 days.

(21) Appl. No.: 16/522,210

(22) Filed: Jul. 25, 2019

(65) Prior Publication Data
US 2021/0023376 A1   Jan. 28, 2021

(51) Int. Cl.
*A61N 1/36*   (2006.01)
*A61N 1/372*   (2006.01)

(52) U.S. Cl.
CPC ..... *A61N 1/36125* (2013.01); *A61N 1/36132* (2013.01); *A61N 1/37235* (2013.01)

(58) Field of Classification Search
CPC ............ A61N 1/36125; A61N 1/36132; A61N 1/37235
See application file for complete search history.

(56) References Cited

U.S. PATENT DOCUMENTS

| | | | |
|---|---|---|---|
| 5,201,865 A | 4/1993 | Kuehn | |
| 5,571,156 A | 11/1996 | Schmukler | |
| 5,645,572 A | 7/1997 | Kroll et al. | |
| 5,741,311 A | 4/1998 | McVenes et al. | |
| 5,944,746 A | 8/1999 | Kroll | |
| 6,236,892 B1 | 5/2001 | Feler | |
| 6,721,600 B2 | 4/2004 | Jorgenson et al. | |
| 6,978,171 B2 | 12/2005 | Goetz et al. | |
| 7,149,580 B2 | 12/2006 | Conley et al. | |
| 7,289,851 B2 | 10/2007 | Gunderson et al. | |
| 7,317,948 B1 | 1/2008 | King | |
| 7,454,249 B1 | 11/2008 | Bornzin et al. | |
| 7,515,961 B2 | 4/2009 | Germanson et al. | |
| 7,574,259 B1 | 8/2009 | Pei et al. | |
| 8,190,258 B2 | 5/2012 | Armstrong | |
| 8,195,294 B2 | 6/2012 | Goetz et al. | |
| 8,355,783 B2 | 1/2013 | Goetz et al. | |
| 8,396,543 B2 | 3/2013 | Hoeppner et al. | |
| 8,463,384 B2 | 6/2013 | Germanson et al. | |
| 8,515,538 B1 | 8/2013 | Osorio et al. | |
| 8,577,457 B2 | 11/2013 | Miller | |

(Continued)

FOREIGN PATENT DOCUMENTS

| | | |
|---|---|---|
| WO | WO9842406 | 10/1998 |
| WO | WO2006017277 | 2/2006 |

(Continued)

OTHER PUBLICATIONS

International Search Report and Written Opinion for PCT/US2020/039483 dated Sep. 10, 2020.

*Primary Examiner* — Ankit D Tejani
*Assistant Examiner* — Joshua Brendon Solomon
(74) *Attorney, Agent, or Firm* — Patterson Thuente Pedersen, P.A.

(57) ABSTRACT

Embodiments disclosed herein relate to systems and methods for detecting faults in leads and automatically reconfiguring a stimulation pattern of the leads based on a detected fault.

25 Claims, 10 Drawing Sheets

(56) References Cited

U.S. PATENT DOCUMENTS

| | | |
|---|---|---|
| 8,583,253 B1 | 11/2013 | Shi et al. |
| 8,644,930 B2 | 2/2014 | Kelly |
| 8,644,931 B2 | 2/2014 | Stadler et al. |
| 8,838,242 B2 | 9/2014 | Goetz et al. |
| 8,855,765 B2 | 10/2014 | Spear et al. |
| 8,868,203 B2 | 10/2014 | Armstrong |
| 8,942,798 B2 | 1/2015 | Armstrong et al. |
| 9,014,807 B2 | 4/2015 | Bocek et al. |
| 9,061,146 B2 | 6/2015 | Gerber |
| 9,399,141 B2 | 7/2016 | Gunderson |
| 9,522,277 B2 | 12/2016 | Gunderson |
| 9,636,500 B2 | 5/2017 | Swerdlow et al. |
| 9,750,932 B2 | 9/2017 | Spear et al. |
| 9,776,006 B2 | 10/2017 | Parker et al. |
| 9,827,416 B2 | 11/2017 | Swerdlow |
| 9,987,485 B2 | 6/2018 | Kroll et al. |
| 10,039,919 B2 | 8/2018 | Kroll et al. |
| 10,080,898 B2 | 9/2018 | Denison et al. |
| 10,118,041 B2 | 11/2018 | Goetz et al. |
| 10,220,204 B2 | 3/2019 | Stanslaski et al. |
| 2002/0128685 A1 | 9/2002 | Hoium et al. |
| 2003/0036772 A1 | 2/2003 | Saphon et al. |
| 2004/0111130 A1 | 6/2004 | Hrdlicka et al. |
| 2005/0090870 A1 | 4/2005 | Hine et al. |
| 2006/0264777 A1 | 11/2006 | Drew |
| 2007/0027653 A1 | 2/2007 | Godara |
| 2007/0265671 A1 | 11/2007 | Roberts et al. |
| 2007/0265674 A1 | 11/2007 | Olson et al. |
| 2008/0103552 A1 | 5/2008 | Goetz et al. |
| 2009/0259216 A1 | 10/2009 | Drew et al. |
| 2009/0299201 A1 | 12/2009 | Gunderson |
| 2009/0326600 A1 | 12/2009 | Kracker |
| 2010/0063561 A1 | 3/2010 | Sloman et al. |
| 2011/0034964 A1* | 2/2011 | Bi .......... A61N 1/025 607/5 |
| 2011/0098766 A1* | 4/2011 | Gunderson .......... A61B 5/0424 607/14 |
| 2011/0112609 A1* | 5/2011 | Peterson .......... A61N 1/36185 607/59 |
| 2012/0191153 A1 | 7/2012 | Swerdlow et al. |
| 2013/0103106 A1* | 4/2013 | Schotzko .......... A61N 1/3686 607/2 |
| 2013/0165987 A1 | 6/2013 | Hareland et al. |
| 2014/0163639 A1 | 6/2014 | Zhu |
| 2017/0219509 A1* | 8/2017 | Bakalos .......... G01N 27/20 |
| 2017/0296810 A1* | 10/2017 | Thakur .......... A61N 1/371 |
| 2018/0071530 A1 | 3/2018 | Giftakis et al. |

FOREIGN PATENT DOCUMENTS

| | | |
|---|---|---|
| WO | WO2006119131 | 11/2006 |
| WO | WO2008027885 | 3/2008 |

* cited by examiner (a)    (b)

SYSTEMS AND METHODS FOR LEAD FAULT DETECTION AND RECONFIGURATION

TECHNICAL FIELD

This disclosure relates generally to therapeutic electrical stimulation and more particularly to detecting faults in leads and reconfiguring a stimulation pattern of the leads based on a detected fault.

BACKGROUND

Neurostimulation leads connect an implantable neurological stimulator (INS) to target tissues in a patient in order to deliver therapeutic stimulation pulses to tissue of interest for the treatment of a wide variety of neurological disorders. Because the leads are mechanical in nature, they are subject to fracture or shorting mechanisms that may lead to a loss of robust electrical continuity between the INS and the target tissue. Such failure modes may result in the failure of the INS to deliver the intended stimulation profile to the patient and lead to a degradation or loss of therapy as well as patient complaints with the system. Failures in the lead pathway may result in the need for a clinician to reprogram the INS to deliver stimulation via a different pathway, or even surgical revision or replacement of the system, each of which is undesired.

SUMMARY

Methods to more accurately predict potential lead failures before they occur and to provide alternative ways of delivering the desired therapy would be advantageous for any stimulation system.

Accordingly, embodiments relate to systems and methods for detecting faults in leads and reconfiguring a stimulation pattern of the leads based on a detected fault.

In one embodiment, a system configured to provide therapeutic electrical stimulation to target tissue comprises a electrical stimulation generator configured to generate electrical stimulation pulses; one or more leads each comprising a plurality of electrodes, the one or more leads electrically coupled with the electrical stimulation generator to deliver the electrical stimulation pulses to the target tissue via the plurality of electrodes; and control circuitry comprising memory storing a stimulation program defining therapeutic electrical stimulation to be generated by the electrical stimulation generator and provided to the at least one of the plurality of electrodes, the control circuitry configured to: control the electrical stimulation generator to generate the electrical stimulation pulses, measure over time impedances of a current pathway associated with at least one electrode of the plurality of electrodes, monitor at least one impedance trend associated with the current pathway, and determine, by applying a predictive model based on the at least one impedance trend and historical lead reliability data, whether the at least one impedance trend is related to a fault in the pathway or a physiological change.

In another embodiment, a pathway integrity monitoring and reconfiguration system for electrical stimulation lead management comprises a stimulation device including one or more leads and configured to provide therapeutic electrical stimulation to target tissue via a plurality of electrodes of the one or more leads; a lead integrity tester coupled to the one or more leads and configured to measure one or more electrical pathway integrity parameters of the one or more leads; a lead integrity memory module coupled to the lead integrity tester and configured to store at least the one or more electrical pathway integrity parameters for each occurrence of measurement of the one or more electrical pathway integrity parameters; and a controller coupled to the one or more leads and the lead integrity memory and configured to control the one or more leads based on a predictive model generated by analyzing the measurements of the one or more electrical pathway integrity parameters over a period of time.

In yet another embodiment, a method of monitoring pathway integrity and automatically implementing pathway reconfiguration in a system comprises delivering electrical stimulation via at least one pathway; measuring an impedance in the system related to delivering at least one pulse via the at least one pathway; storing, via circuitry of the system, the measured impedance for a plurality of pulses and identifying at least one trend in the stored measured impedances; storing historical data via the circuitry; storing instructions via the circuitry for a predictive model to utilize the at least one trend and the historical data; and generating, via the system, an output when application of the predictive model determines that the at least one trend is related to a fault in one or more of the at least one pathway.

The above summary is not intended to describe each illustrated embodiment or every implementation of the subject matter hereof. The figures and the detailed description that follow more particularly exemplify various embodiments.

BRIEF DESCRIPTION OF THE DRAWINGS

Subject matter hereof may be more completely understood in consideration of the following detailed description of various embodiments in connection with the accompanying figures, in which.

Figure 1:
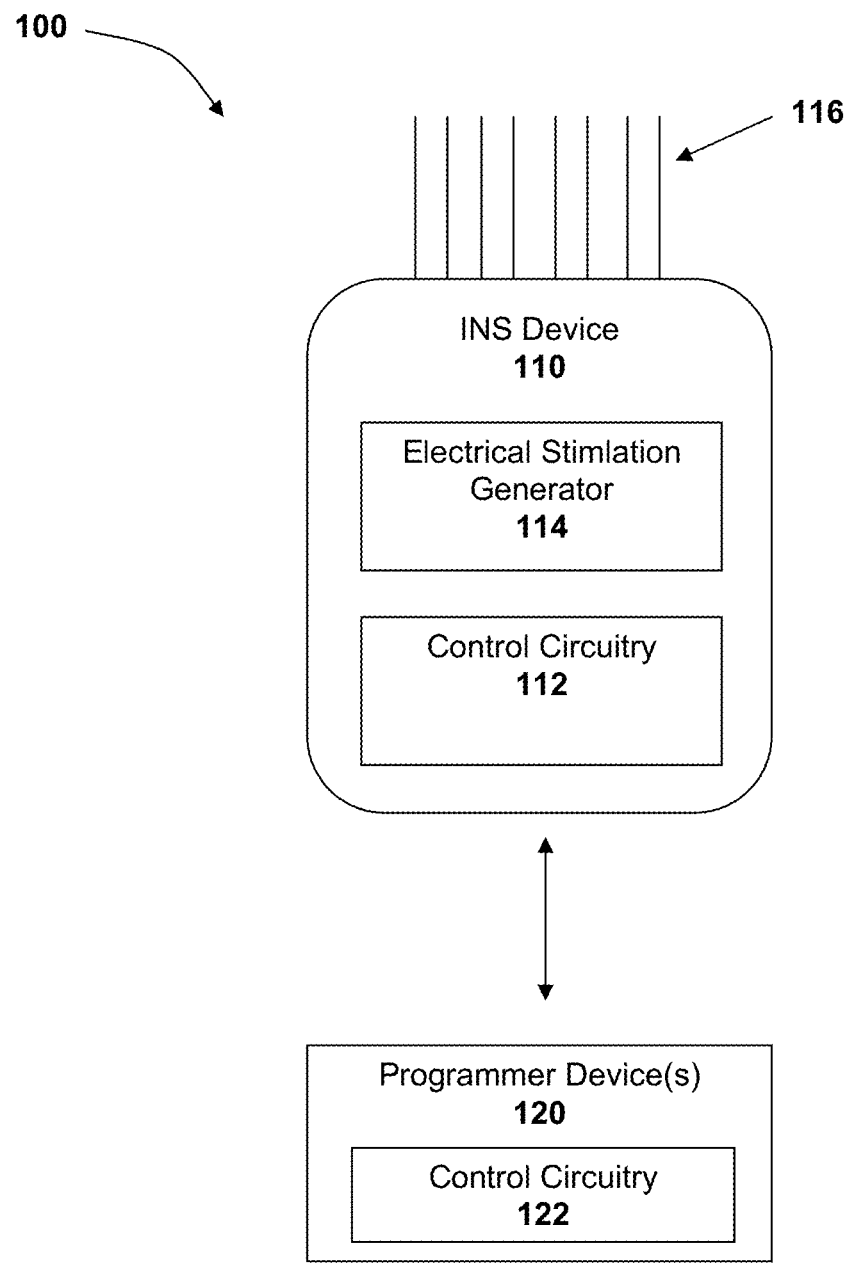
FIG. 1 depicts a block diagram of a stimulation system according to an embodiment.

While various embodiments are amenable to various modifications and alternative forms, specifics thereof have been shown by way of example in the drawings and will be described in detail. It should be understood, however, that the intention is not to limit the claimed inventions to the particular embodiments described. On the contrary, the intention is to cover all modifications, equivalents, and alternatives falling within the spirit and scope of the subject matter as defined by the claims.

DETAILED DESCRIPTION OF THE DRAWINGS

Embodiments disclosed herein relate to systems and methods for detecting faults in leads and automatically reconfiguring a stimulation pattern of the leads based on a detected fault. Though embodiments have applicability to a wide variety of systems, one example depicted and discussed herein relates to a neurostimulation system, such as an implantable neurostimulation system. This example is not limiting with respect to other types of neurostimulation, stimulation more generally, or other systems using leads and in which fault detection has relevance.

Referring to FIG. 1, an embodiment of an electrical stimulation system 100 is depicted. Electrical stimulation system 100 can comprise any of a variety of different types of stimulation systems, and the example of a neurostimulation system will be used herein for convenience. Accordingly, neurostimulation system 100 will be referred to going forward but is not limiting with respect to the various types of electrical stimulation devices the system may comprise or embody.

In one embodiment, neurostimulation system 100 comprises an implantable neurological stimulator (INS) device 110 and a programmer device 120. INS device 110 comprises control circuitry 112, an electrical stimulation generator 114, and leads 116, as well as other components appreciated by those skilled in the art though not explicitly discussed herein (e.g., power supply, such as a replaceable or rechargeable battery). In some embodiments, INS device 110 is implantable, surgically placed under the skin of a patient (such as in the abdomen or lower back/upper buttock to deliver electrical signals to the epidural space near the spine through leads 116, or with pectoral or cranial mounting for other therapy modalities). In various embodiments, the portions of neurostimulation system 100, including portions of INS device 110, that are implanted or implantable can vary. In one embodiment, all of INS device 110 as depicted in FIG. 1 can be implanted. In another embodiment, only a portion of INS device 110 as depicted in FIG. 1 may be implanted, with some portion of INS device 110 being not implanted. For example, INS device 110 may be worn partially externally by a patient, with only some or all of the length of leads 116 implanted under the skin of the patient. In still other embodiments, some portions of INS device 110 may have implanted and external components, such as control circuitry 112, which may be divided such that a portion is implanted or implantable while another portion remains external to the patient. In one particular example, control circuitry 112 comprises a control circuitry portion and a measurement circuitry portion, and the control circuitry portion is external while at least some of the measurement circuitry portion is implanted or implantable.

Neurostimulation system 100 can deliver spinal cord stimulator (SCS) therapy to a patient in order to, for example, reduce pain experienced by the patient. In another embodiment, such stimulation can be delivered to areas around the spine to provide cardioprotection related to detection of onset of ischemia. In still another embodiment, such stimulation can be provided in relation to heart failure. In yet another scenario, one or more leads 116 can extend to the brain and may deliver deep brain stimulation (DBS) therapy to a patient to, for example, treat tremor, Parkinson's disease, or epilepsy. As further examples, one or more leads can be implanted proximate to the pelvic nerves, stomach, or other organs and can deliver neurostimulation therapy to treat incontinence, gastroparesis, sexual dysfunction or other disorders. In another embodiment, INS 110 device can comprise or provide another type of therapy, such as cardiac therapy to deliver stimulation to the heart.

Control circuitry 112 comprises communication and other circuitry configured to communicate with programmer device 120, in particular to receive stimulation programs and other instructions and send data and other information. Control circuitry 112 also comprises memory and a microcontroller configured to store stimulation programs and other information and to control electrical stimulation generator 114 to generate stimulation programs, which can comprise one or a series of pulses, to be delivered to a patient's tissue by leads 116 and/or to control receiving physiological signal data that is sensed from the patient via leads 116 or other sensors.

Electrical stimulation generator 114 is operatively coupled to leads 116, wired or wirelessly. For example, electrical stimulation generator 114 and leads 116 can be coupled physically, electrically, inductively, via radio frequency, using midfield coupling, or using another suitable wired or wireless coupling such that generated patterns of electrical pulses or continuation waveform patterns that are generated by electrical stimulation generator 114 are communicated and delivered to a patient's tissue by one or more of leads 116.

Figure 2:
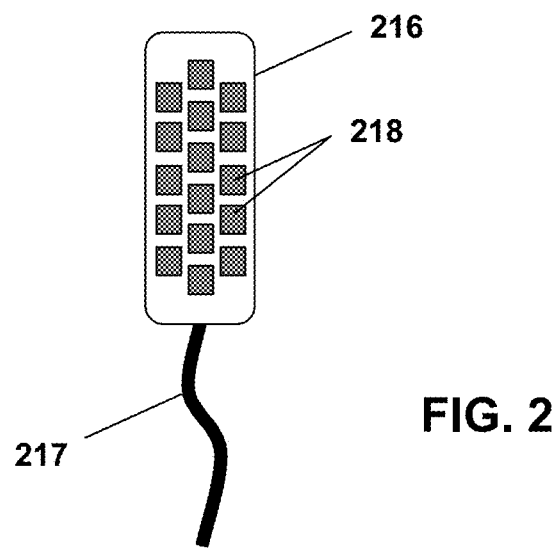
FIG. 2 depicts a lead and electrodes of a stimulation system according to an embodiment.

Each lead 116 comprises a thin, insulated medical wire and at least one electrode 218. In the embodiment of FIG. 2, an example lead 216 comprises wire 217 and a plurality of electrodes 218, specifically 16 electrodes. In other embodiments, leads 116, 216 can comprise more or fewer electrodes, or different patterns or arrangements of electrodes. Multiple leads 116 associated with one INS device 110 need not comprise the same number of electrodes 218. Additionally, other electrode 218 configurations are possible. For example, leads 116, 216 can comprise an elongated wire 217 with electrodes 218 arranged along the length of the wire and optionally around the circumference of the wire. For example, leads 116, 216 can be cylindrical in shape and carry one or more ring electrodes that completely encircle the circumference of the lead body and/or can carry one or more segmented electrodes (e.g., that do not encircle the entire lead body) that are located at one or more angular and axial positions on the lead body.

In use, electrical pulses generated by electrical stimulation generator 114 travel through wire 217 and are delivered to a patient's tissue by electrode(s) 118. Stimulation programs comprise patterns of pulses or continuation waveforms that are delivered via particular ones of leads 116 (or particular electrodes 218 of particular leads 216) to provide desired therapies to a patient. As previously mentioned, control circuitry 112 communicates with programmer device 120 to receive stimulation programs and other instructions for operation of INS device 110. In some embodiments, communications between INS device 110 and programmer device 120 are wireless, and in other embodiments the communications are wired. In still other embodiments, INS device 110 and programmer device 120 comprise both wired and wireless circuitry such that a user can select a desired or suitable communication methodology.

Programmer device 120 can include one or more of several different types of programming devices. For example, programmer device 120 can comprise an initial programmer device that provides factory settings and other basic programs and information to INS device 110. Programmer device 120 also can comprise a professional programming device used by a clinician to program or reprogram INS device 110.

Further, programmer device 120 can comprise a patient programmer device used by a patient to adjust settings or otherwise control stimulation as well as to provide feedback regarding received therapies. Symptoms (such as pain, tremors or episodes) experienced by a patient can move, intensify or otherwise be altered as the patient changes positions. The patient may have the ability to adjust the intensity of the delivered stimulation to address these changes in symptoms. For example, if symptoms worsen at different times of the day or during various activities—such as walking, sleeping, or sitting—the patient can accommodate these changes with by adjusting the intensity or periodicity of stimulation via programmer device 120.

In various embodiments, programmer device 120 can comprise one or more of a dedicated handheld device, a computer (such as a desktop or laptop), a mobile device (for example a tablet, smart phone or other smart device, such as a watch, bracelet, necklace, or fob) running an application ("app") or containing other software, or some other device capable of communicating with INS device 110. Programmer device 120 comprises a user interface via which a user can enter or receive information. The user interface can include one or more of a screen, touchscreen, button, smart button, wheel, pad, mouse, trackpad, stylus, electronic pencil, or some other device by which a user can receive information about or provide information too programmer device 120.

Programmer device 120 also can comprise control circuitry 122. Control circuitry 122 can control operation of programmer device 120, including the user interface. In some embodiments, control circuitry 122 communicates with control circuitry 112 of INS device 110 to send stimulation programs and other instructions for operation of INS device 110. For example, in some embodiments stimulation programs can be stored in programmer device 122, and instructions for operation (rather than programs themselves) can be resident on, executed by or sent from control circuitry 122 of programmer device 120 to control circuitry 114 and electrical stimulation generator 114 of INS device 110 during operation. In other words, programs and instructions need not reside, partially or completely, on INS device 110 in some embodiments. In various embodiments, these programs and instructions, as well as other information, can reside on or be controlled by programmer device 120 or some other device external to or remote from both INS device 110 and programmer device 120. Communications between any devices in neurostimulation system 100 can be wireless in some embodiments, while in other embodiments the communications can be wired. In still other embodiments, devices in neurostimulation system 100 can comprise both wired and wireless circuitry such that a user can select a desired or suitable communication methodology.

For any particular patient, a stimulation profile electrode configuration typically is determined or programmed by a clinician in order to achieve a desired or optimal clinical response for the patient. Desired or optimal responses may not be obtained, however, if one or more of leads 116 fail. Thus, in embodiments control circuitry 112 (and/or circuitry external to INS device 110, in communication with INS device 110 via programmer device 120) can carry out real-time or periodic monitoring of stimulation pulses delivered from INS device 110 to the patient.

In embodiments, INS device 110 (via electrical stimulation generator 114) provides either a programmed (fixed) voltage or programmed (fixed) current stimulation pulse train to the tissue, such that a corresponding delivered current (for fixed voltage stimulation) or voltage (for fixed current stimulation) can be measured to gauge an efficacy of the stimulation output. In the event of a conductor fracture in one of leads 116, which would manifest itself as an increase in conductor impedance, a constant voltage stimulation pulse would result in a decrease in delivered current. Likewise, a constant current stimulation pulse would result in an increase in the voltage of the delivered pulse. Conversely, if a short between two conductors involved in the electrical stimulation exists in neurostimulation system 100, there would be a corresponding decrease in the pathway impedance, which would result in an increase in current for a fixed voltage stimulation pulse or a decrease in voltage for fixed current stimulation pulse. Still other faults and problems with leads 116 can result in a detectable change in impedance.

Thus, when the current and voltage are monitored over time, a view of the change in the delivery impedance can be analyzed. The pathway impedance will be affected by both physical changes in neurostimulation system 100 as well as natural variations in impedance from physiological changes in the tissue impedance between anode and cathode stimulation electrodes 218 on the lead 116, 216. Physiological changes in tissue impedance can occur due to patient posture, hydration levels, electrolytic balance, activity, and other characteristics or conditions. In a normally functioning neurostimulation system 100 with no lead pathway integrity issues, natural physiological changes will dominate impedance changes while the intrinsic impedance of neurostimulation system 100 will not vary. However, if lead pathway issues begin to emerge, there will eventually be a change in impedance that may be detectable and actionable, either for clinical utility or potential automatic reconfiguration of the therapy pathway. It is this change in impedance that neurostimulation system 100 aims to detect and act upon.

As mentioned above, a stimulation profile electrode configuration can be programmed in neurostimulation system 100 by a clinician in order to achieve a desired or optimal clinical response for a patient, and the patient may have the ability to adjust the intensity of the delivered stimulation via the programmed electrode configuration profile, using programmer device 120. During therapeutic use, embodiments disclosed herein include a method of monitoring the impedance of stimulation pathways as well as conducting tests of the pathway impedance of potential alternative electrode configurations and pathways. This evaluation of potential alternative electrode configurations can take place during normal clinical use of neurostimulation system 100 without impacting the therapeutic benefit desired by the clinician and patient. As many stimulation profiles operate at relatively high frequency relative to the time period of perceived clinical benefit, an occasional alternation of the stimulation pathway can be useful.

Figure 3:
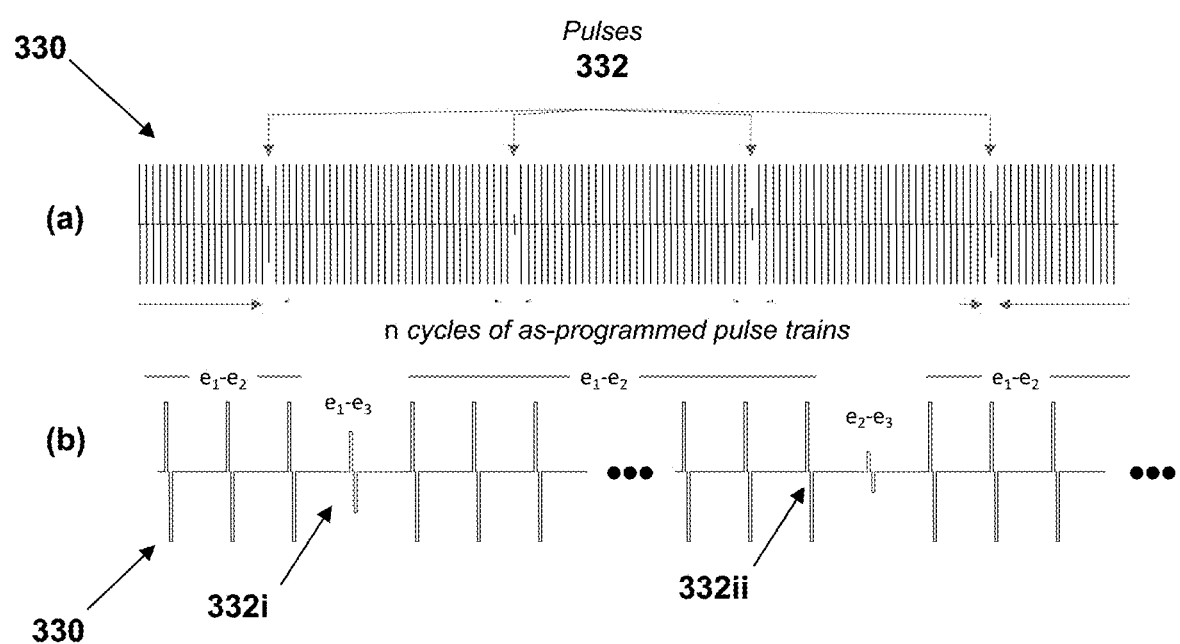
FIG. 3 depicts two electrical stimulation pulse trains according to an embodiment.

This is illustrated in FIG. 3, in which a normal clinical stimulation profile 330 at (a), as programmed by a clinician, is interrupted by at least one pulse 332 for an alternative pathway impedance test. Put another way, pulses 332 are initiated during a normal clinical stimulation profile and need not be considered an interruption per se. Pulses 332 can be individual, repetitive, periodic, random, on-demand, or executed according to some other arrangement. A zoomed-in depiction of a portion of (a) is shown at (b). The frequency, pulse width, amplitude, and other characteristics of pulses 332 can be programmed and stored in control circuitry 112 for implementation by electrical stimulation generator 114.

Figure 4:
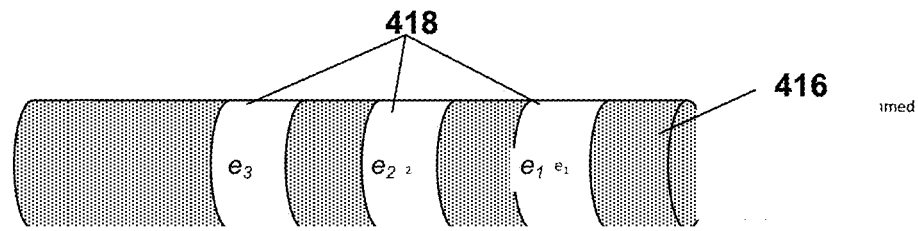
FIG. 4 depicts a lead and electrodes of a stimulation system according to an embodiment.

Over time, the impedance of both a desired electrode configuration as well as alternative pathways can be collected. Even though the sampling frequency may be quite different, it is relatively easy to monitor trends in impedance over time. The alternative electrode pathways that are periodically sampled can be set up in such a way so as to test the impedance of each electrode, such that a change in impedance can be identified for any particular electrode. Referring to FIG. 4, a lead 416 comprises three electrodes 418, also referred to as $e_1$, $e_2$ and $e_3$. Electrode $e_1$ is the distal electrode and electrode $e_3$ is the proximal electrode, both with respect to neurostimulation system 100. In the example embodiment of FIG. 3, the clinically programmed electrode configuration is for electrodes $e_1$ and $e_2$ ($e_1$-$e_2$), and periodic alternative pathways to be checked include $e_1$-$e_3$ (332i) and $e_2$-$e_3$ (332ii) in addition to reverse polarity checks (by swapping the anode and cathode).

Figure 5:
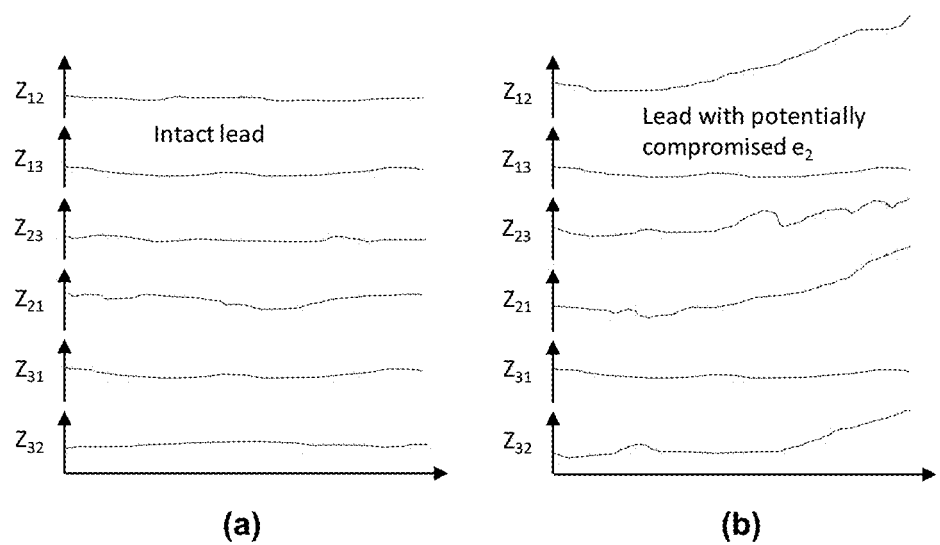
FIG. 5 depicts impedance measurement trends over time according to an embodiment.

If the conductor to electrode $e_2$ is compromised, the $e_1$-$e_2$ and $e_2$-$e_3$ pathways will reflect an impedance change while the $e_1$-$e_3$ pathways should not. Thus, this overlapping electrode configuration pathway testing can help to identify particular potential lead pathway faults. If two electrodes are shorted together, then the test of that pair would result in a drop in the impedance on that pathway compared to other pathways as well as the historical trend. These trends can be stored in and tracked by control circuitry 112, programmer device 120 or some other component or device within or external to neurostimulation system 100. FIG. 5 shows, at (a) an example impedance trend for an intact lead as well as, at (b) the impedance trend for an example lead with a compromised lead pathway (on $e_2$) as identified by increasing impedance when $e_2$ is involved in the impedance (Z) measurements.

This approach can be extended to lead pathways with many more electrodes (refer again to the example lead 216 of FIG. 2, which includes 16 electrodes 218) and programming options. Not all pathway combinations have to be checked since that can quickly escalate into a complex program when more than a few electrodes 218 are involved. Rather, in some embodiments an impedance checking algorithm can be implemented to sweep through a sufficient number of electrode configurations, such as one in which each electrode is tested at least once in a configuration, in order to help identify one or more electrodes that may have compromised electrical pathways.

Figure 6:
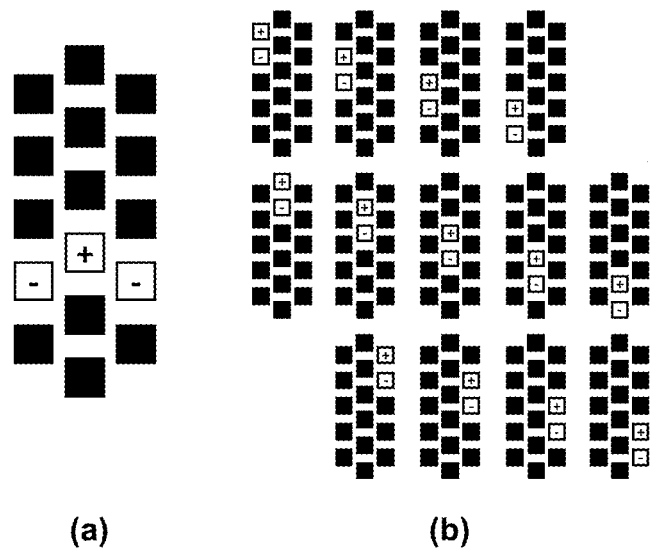
FIG. 6 depicts programmed and periodic electrode impedance check pathways according to an embodiment.

Referring to FIG. 6, an example programmed configuration of electrodes 218 is shown at (a), and at (b) a range of two-electrode configurations are identified for periodic, non-therapy-impacting impedance checks and monitoring on a 16-electrode lead configuration. Referring also to FIG. 3, in one embodiment the two-electrode configurations shown in FIG. 6 can be cycled through by applying a series of test pulses 332 for each configuration, periodically within the programmed configuration of (a). In this way each of the 16 electrodes can be checked and, from the various configurations, the impedance checking algorithm can identify one or more electrodes that may have compromised electrical pathways.

In order to accurately determine if a particular lead pathway may be compromised, in various embodiments neurostimulation system 100 implements a predictive model or machine learning approach. Predictive models use statistics to predict outcomes or events. These outcomes or events often are future events, but in some situations predictive models can be used to identify events that have already occurred but have not been recognized or for which causes or responsibility are not known. In various embodiments discussed herein, predictive models can be used to determine whether a lead pathway may be compromised and, if a likely-compromised pathway is identified, to identify an alternate pathway to use.

Many different types of predictive models exist and can be used in various embodiments of neurostimulation system 100. In one embodiment, a Bayesian Network model is used. Bayesian Network models are probabilistic graphical models that represent a set of variables and the conditional dependencies of the variables in a directed acyclic graph. In other embodiments another predictive model or statistical or machine learning approach may be utilized. In general, the predictive model is selected so as to maintain both high sensitivity and high specificity. Any notification to a clinician about potential lead compromise needs to balance timely notification with minimization or avoidance of false-positives, which can lead to unwarranted clinical concern and possible unnecessary surgical revision of neurostimulation system 100.

Figure 7:
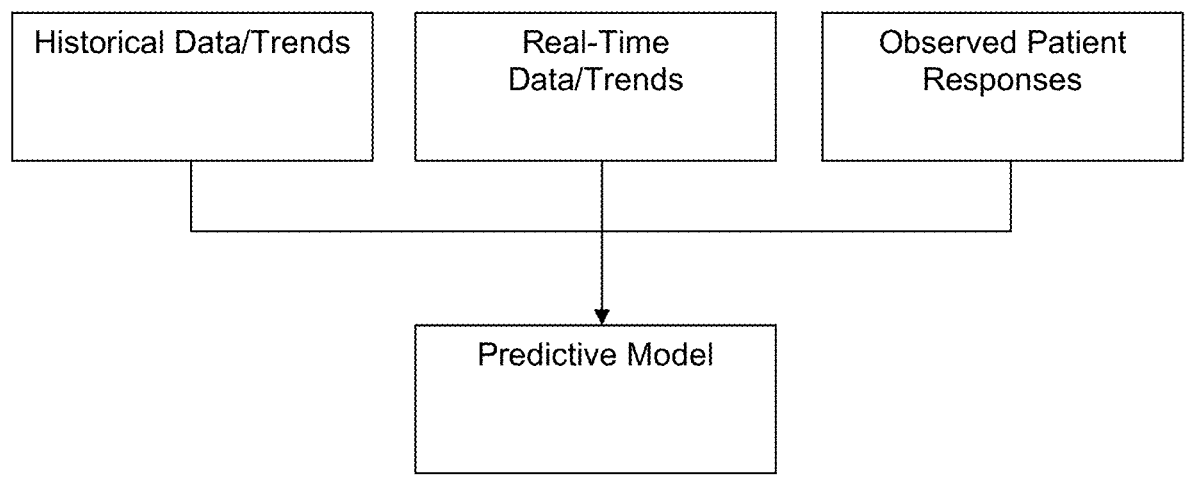
FIG. 7 depicts a block diagram of potential inputs to a predictive model according to an embodiment.

Referring to FIG. 7, and in an embodiment utilizing a predictive model (such as a Bayesian Network), the predictive model can utilize both historical and real-time data/trends in impedance changes as well as optionally considering observed patient responses. Historical data can include historical lead reliability data, which can relate to the probability of failure of a lead as a function of expected useful life of the lead. Data also can include a historical assumption of integrity over time of a lead and electrode pathway, which can include one or more of a beginning of lead life assumption, a useful lead life assumption, or an end of lead life assumption. Additionally, since patients can alter the stimulation intensity to help optimize the therapy, changes in stimulation profile intensity also can also be used as data points or evidence. For example, if a lead conductor fracture results in the loss of adequate stimulation, a patient may respond by attempting to increase the stimulation intensity. This behavior, along with the impedance measurements, can provide even more evidence to the Bayesian or other predictive analysis to more accurately predict true vs. false-positive signals. Additionally, Bayesian Network models can include more inputs or different model structures than those shown in FIG. 7 or depicted or discussed elsewhere herein. Though many different predictive models can be used, examples given herein will refer to Bayesian Networks.

A Bayesian Network (also referred to as a Bayesian Belief Network) is a probabilistic graphical model that represents an explicit description of the direct dependencies among a set of variables. This description is in the form of a directed acyclic graph and a set of Node Probability Tables.

In a Bayesian network, there are nodes and arcs. An arc from node A to node B indicates that B directly depends on A. Cycles are not allowed in a Bayesian network in order to avoid circular reasoning. For example, since there is one arc from node A to node B, and another arc from B to node C, then there shall be no arc from node C to node A.

Figures 8, 9, 10:
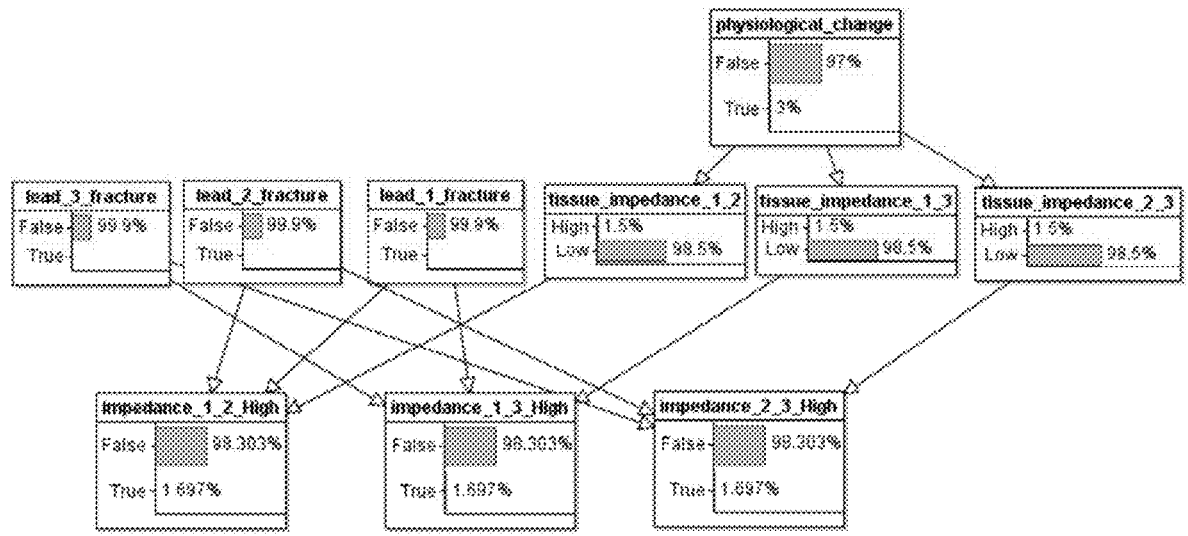
FIG. 8 depicts a Bayesian Belief Network according to an embodiment.
FIG. 9 depicts a node probability table associated with a node of the Bayesian Belief Network of FIG. 8.
FIG. 10 depicts an expression for a node of the Bayesian Belief Network of FIG. 8.

Referring to FIG. 8, an example Bayesian Network model to diagnose lead conductor factures for a three-electrode lead (such as lead 416 depicted in FIG. 4) is illustrated. It is assumed that the conductor of each of the three electrodes (418) has a probability of fracture of 0.1%, 1%, and 5% at the beginning of life, during its useful life, and at the end of life, respectively. These a priori or historical assumptions, including the type of assumption and the associated probability, can vary in other embodiments. The assumptions typically are based on data but in some situations can be pure assumptions. These assumptions or probabilities are used as historical data in the Bayesian Network model. Based on the above fracture rates, the corresponding total lead reliability is 99.7%, 97.0%, and 85.7% for a three-electrode lead at the beginning of life, during its useful life, and at the end of life, respectively, and the corresponding total lead reliability is 98.4%, 85.1%, and 44.0% for a sixteen-electrode lead at the beginning of life, during its useful life, and at the end of life, respectively.

In the Bayesian Network model in FIG. 8, another piece of historical data is the probability of patient physiological change. In one example, this probability is assumed to be 3% and is shown as the probability of being True for node "physiological_change." Node "physiological_change" has three child nodes, which directly depend on "physiological_change": "tissue_impedance_1_2," "tissue_impedance_1_3," and "tissue_impedance_2_3."

FIG. 9 shows how node "tissue_impedance_1_2" depends on "physiological_change": When there is no physiological change, tissue impedance from electrode $e_1$ to electrode $e_2$ will remain low 100% of the time; and when there is physiological change, this tissue impedance will become high or remain low, and each of these two states has a 50% chance of occurring.

Similarly, FIG. 10 shows the expression for node "impedance_1_2_High," which indicates how node "impedance_1_2_High" depends on its three parent nodes. This expression means that if there is fracture of the lead conductor of electrode $e_1$, fracture of the lead conductor of electrode $e_2$, or if the tissue impedance between electrodes $e_1$ and $e_2$ are high due to physiological change, then the measured impedance between electrodes $e_1$ and $e_2$ will show as high impedance.

Figure 11:
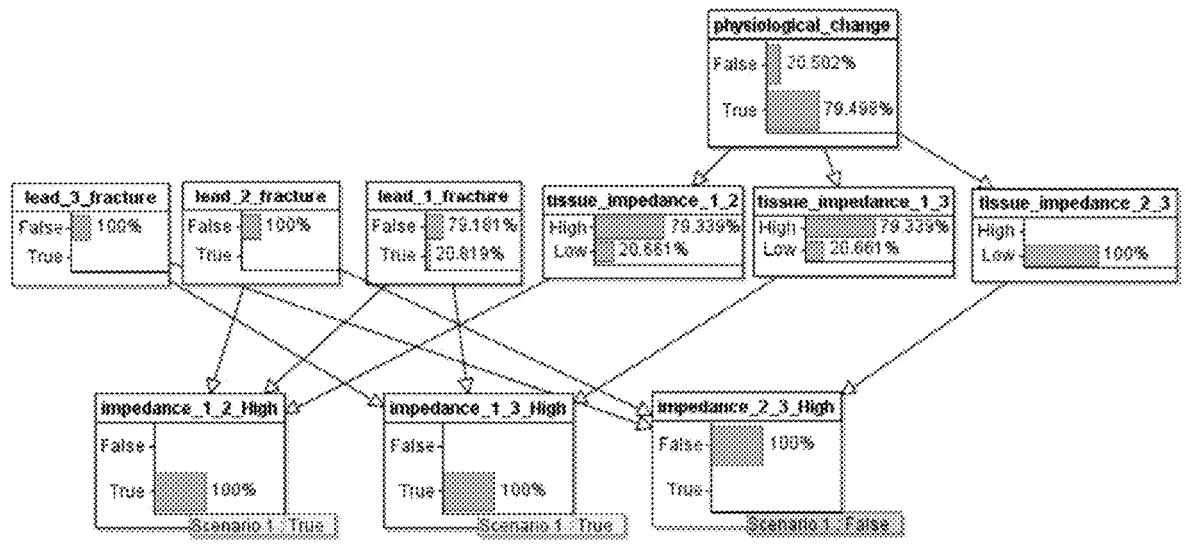
FIG. 11 depicts another Bayesian Belief Network according to an embodiment.

FIG. 11 gives an example of posterior probabilities when several evidences are observed: 1) $Z_{12}$ is high, 2) $Z_{13}$ is high, and 3) $Z_{23}$ is normal. If the measured impedance between electrodes $e_1$ and $e_2$ and between electrodes $e_1$ and $e_3$ are abnormally high, but the impedance between electrodes $e_2$ and $e_3$ is normal, the probability of the lead conductor of electrode $e_1$ being compromised rises from the prior probability of 0.1% to the posterior probability of 21% (noting that it is still more likely that the lead conductor of electrode $e_1$ has not fractured). FIG. 11 also shows that the probability of the lead conductor of electrodes $e_2$ or $e_3$ being fractured is zero based on these evidences. The posterior probability of physiological change is now 79%, meaning that when the same evidences are observed, 79% of the time the real cause for these impedance changes is physiological change in the patient rather than lead fault.

Figure 12:
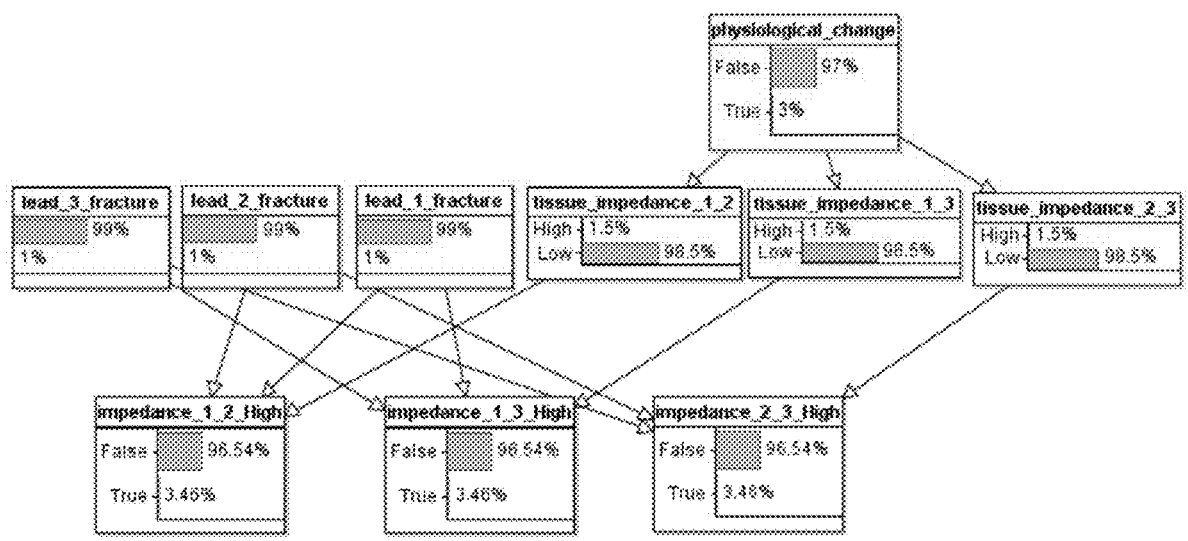
FIG. 12 depicts another Bayesian Belief Network according to an embodiment.
Figure 13:
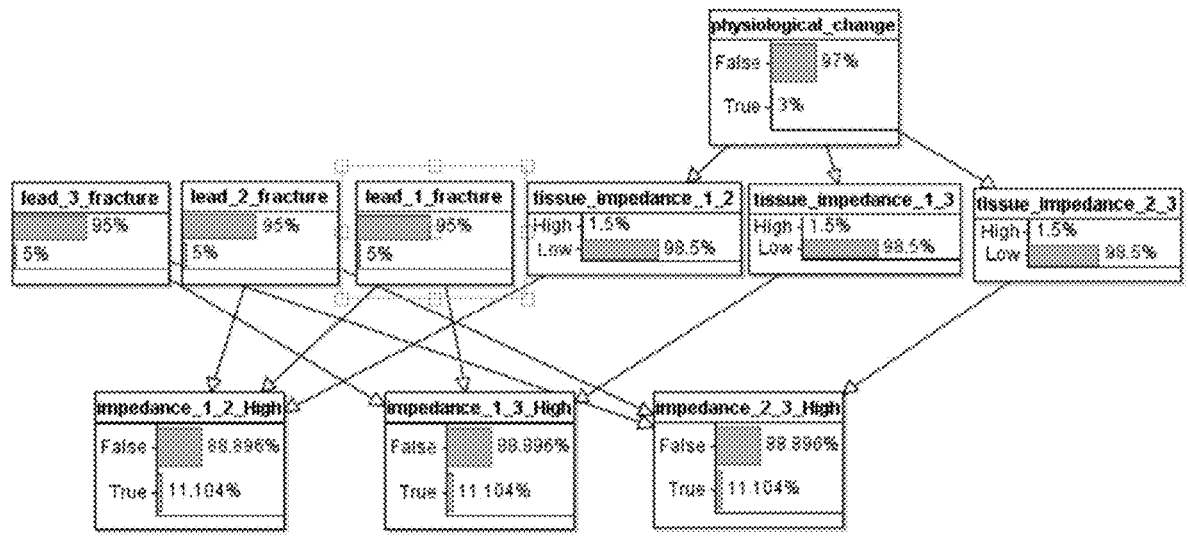
FIG. 13 depicts another Bayesian Belief Network according to an embodiment.
Figure 14:
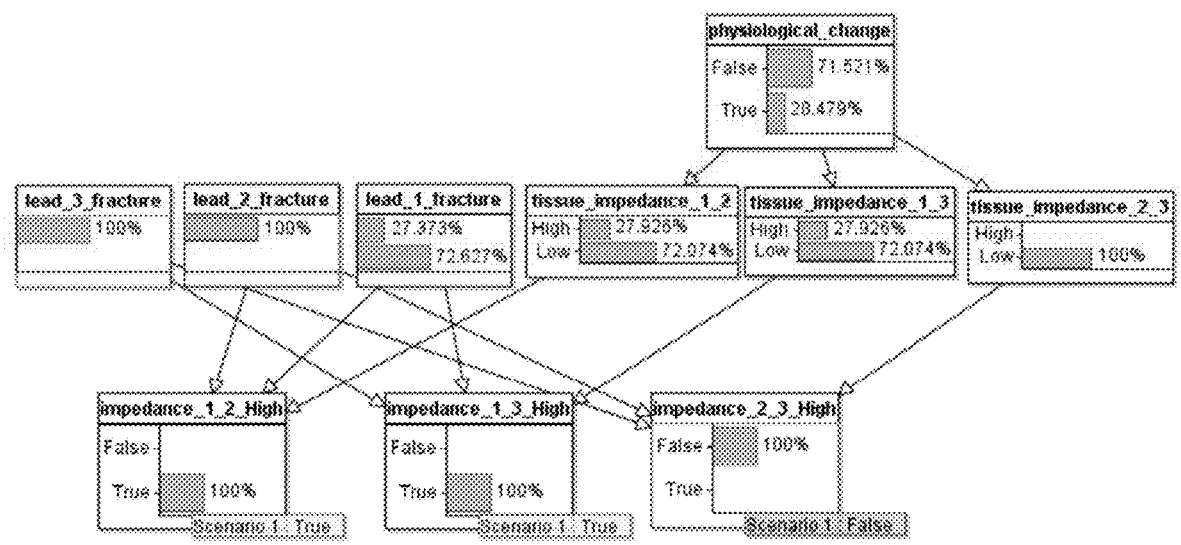
FIG. 14 depicts another Bayesian Belief Network according to an embodiment.
Figure 15:
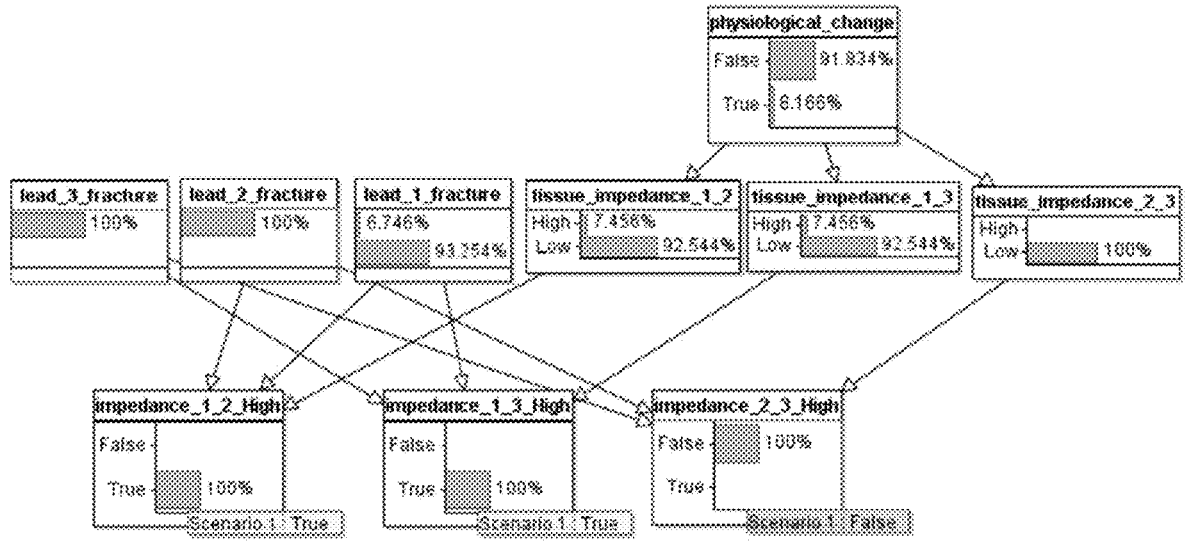
FIG. 15 depicts another Bayesian Belief Network according to an embodiment.

Similarly, Bayesian Network model examples with different conductor fracture probabilities for the useful life and the end of life are shown in FIGS. 12 and 13, respectively. In FIG. 12, the lead fracture probability is 1%, and in FIG. 13 the probability of fracture of lead 1 is 5%, and the probability of physiological change accounting for the change in impedance is 28%. The posterior probabilities given the same observed evidences, which indicate the probabilities of different root causes, are shown in FIGS. 14 and 15, for the useful life and end of life, respectively. For the useful life (assuming the following evidences are observed: 1) $Z_{12}$ is high, 2) $Z_{13}$ is high, and 3) $Z_{23}$ is normal), the probability of lead 1 fracture is 73%, and the probability of physiological change is 28%. For the end of life (assuming the following evidences are observed: 1) $Z_{12}$ is high, 2) $Z_{13}$ is high, and 3) $Z_{23}$ is normal), the probability of lead 1 fracture is 93%, and the probability of physiological change is 8%.

From these examples, it can be seen that when observing the same high impedances, at the beginning of (lead) life the majority of the cases are due to patient physiological changes, while at the end of (lead) life the majority of the cases are due to lead fractures. The Bayesian Network model also indicates which lead conductor is most likely to be compromised given observed evidences. It shows that when the lead fracture rate is higher at the end of life, this approach can be used for lead fracture diagnosis and decision making for subsequent reconfiguration for fault tolerance purposes. At the beginning of life this approach can be used to reduce or avoid unnecessary anxiety from patients due to a high false alarm rate. In general, the more evidences that are given and considered, the higher the posterior probability is.

The overall sensitivity and specificity of neurostimulation system 100 also needs to be assessed and optimized to reduce false-positive and other unnecessary errors. This is illustrated in the following example, which like the above example also applies a Bayesian Network model.

A multiple-sensor system is designed to identify whether a product is defective. The term "sensor" is used here for all ways to detect, measure, or record a signal. Thus, impedance measurement can be considered as one type of sensor. A signal recording indicating whether patients increase stimulation amplitude also can be viewed as a sensor signal. The initial assumption is that probability of fault is 1%. The sensitivity and specificity of each sensor are assumed to be 95% for illustration purposes. Additionally, the sensors are assumed to be independent of one another in this example.

Consider the following different design options:
(1) There is only one sensor in the system. The system is claimed to be defective when a fault is detected by the sensor.
(2) There are two independent sensors in the system. The system is claimed to be defective when a fault is detected by both sensors.
(3) There are three independent sensors in the system. The system is claimed to be defective when a fault is detected by all three sensors.
(4) There are three independent sensors in the system. The system is claimed to be defective when a fault is detected by two out of the three sensors.

In order to choose the best design among the options (1)-(4), the sensitivity, specificity, Positive Predicted Value (PPV), and Negative Predictive Values (NPV) can be calculated for each of the system design options. The definitions of these terms are as follows:
Sensitivity=P(identified fault|fault),
Specificity=P(identified success|success),
PPV=P(fault|identified fault), and
NPV=P(success|identified success).

Ideally the sensitivity, specificity, PPV, and NPV in a system all are high. Per Bayes' Theorem, the system's sensitivity, specificity, PPV and NPV of the remaining design options were calculated in this example, and the results are shown in Table 1.

TABLE 1

| Option | Fault Detection Triggered By | Sensitivity | Specificity | PPV | NPV |
|---|---|---|---|---|---|
| 1 | 1 sensor | 95% | 95% | 16.1% | 99.9% |
| 2 | 2 sensors | 90.3% | 99.8% | 78.5% | 99.9% |
| 3 | 3 of 3 sensors | 85.7% | 99.99% | 98.6% | 99.9% |
| 4 | 2 of 3 sensors | 99.3% | 99.3% | 58.0% | 99.99% |

Results of option (1) indicate the PPV is too low (only 16.1%). This means that option (1) will result in a large proportion of false alarms. When including more independent sensors/evidences in the system to detect fault, PPV is greatly increased but sensitivity decreases as a cost. For example, compared to option (1), option (3) has a much better PPV but a lower sensitivity. This means that when all three sensors detect fault, there is a 98.6% chance that it is truly a defective part. On the other hand, when there is truly a defective part, there is only an 85.7% chance that this defect can be identified by all the three sensors, when using option (3).

None of the four proposed design options provides a system level sensitivity, specificity, PPV, and NPV all being greater than 90%. But if a fifth option, which is modified from option (3) by increasing each sensor's sensitivity to 99%, is added, it is possible to have the system level sensitivity, specificity, PPV, and NPV all being greater than 90%, as shown in Table 2.

TABLE 2

| Option | Fault Detection Triggered By | Sensitivity | Specificity | PPV | NPV |
|---|---|---|---|---|---|
| 5 | 3 of 3 sensors | 97% | 99.99% | 98.7% | 99.97% |

Besides Bayesian Network models, other statistical, predictive model, and machine learning methods can be used for diagnosis or decision making. Generally, there are two ways to build the predictive model for fault diagnosis. The first one is based on design mechanisms, or first principles. The Bayesian Network models introduced above are based on design mechanisms (e.g., when there is a fracture conductor, high impedance of that pathway will be observed, based on physics), and thus such models can be pre-built based on design during the product development phase. Decision tree is another method to build such models. The second way is to build an empirical predictive model based on previously collected implantable device data from sensors (e.g., customer behaviors, impedance signals) and conclusions of failure root causes when each of the monitored implanted devices is explanted, sent back to manufacturer, and has completed root cause analysis. Methods like binary logistic regression, neural networks, and others can be used to build the empirical model. These examples are not exhaustive, and those of skill in the art will recognize that there could be other methods to build first principle or empirical models, or other predictive models or methods that can be used. Nevertheless, several of these other analytical methods are discussed below: decision tree, logistic regression and neural networks.

Decision Tree

Figure 16:
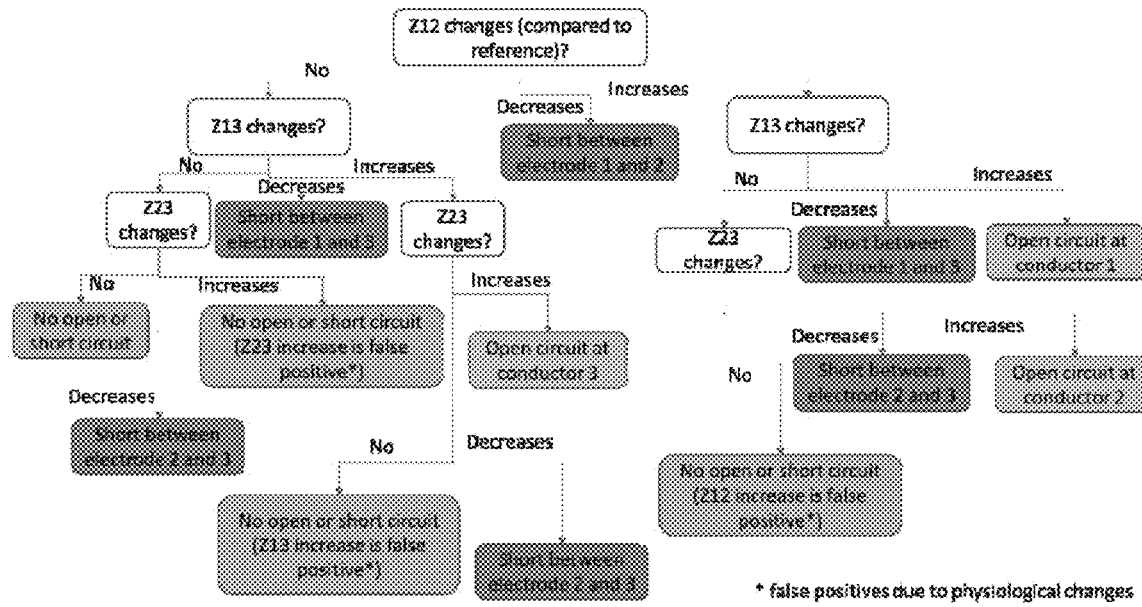
FIG. 16 depicts a decision tree according to an embodiment.

A decision tree is a decision support tool that has a flowchart-like structure in that it has only splitting paths but no converging paths. A decision tree fault diagnosis example is given in FIG. 16. As can be seen in FIG. 16, the decision tree sets out queries, and a path through the tree is defined by answers to the queries. For example, if the impedance $Z_{12}$ changes as compared to a reference value by decreasing, then a short may be identified between electrodes $e_1$ and $e_2$. If instead impedance $Z_{12}$ is observed to increase, then the impedance $Z_{13}$ is observed, and so on.

Binary Logistic Regression

Binary logistic regression is used to build a relationship between a binary response (i.e., the response has two categories, such as yes (1) or no (0)) and one or more predictors. Binary logistic regression is commonly used for pass/fail or event/no-event types of cases. The following summarizes basic equations behind binary logistic regression when there is only one continuous predictor.

Let x be a continuous predictor. Let a response Y be whether or not there is a fault condition, i.e., $Y_i=0$ or 1 (1 indicates an event that could be open circuit condition or short circuit condition, and 0 indicates non-event; i=1, ..., n, where n is the sample size).

Let $P_i$ be the event probability of the i-th part. $Y_i$ is assumed to be Bernoulli distributed. The event probability $P_i$ can be calculated as:

$$P_i = \exp(Y_i')/(1+\exp(Y_i')),$$

where, $$Y_i' = \beta_0 + \beta_1 x_i, \text{ and}$$

$\beta_0$ and $\beta_1$ are unknown coefficients in the linear regression equation between $Y_i'$ and $x_i$.

By building a binary logistic regression, probability of a binary response (e.g., a conductor fracture in this case) can be estimated for a given set of predictor values.

Neural Networks

Similar to linear or logistic regression, neural networks are other ways to build empirical transfer functions between input and output variables. A neural network model includes an input layer, hidden layer(s), and an output layer. Neural networks have the advantages of modeling extremely non-linear phenomena and being useful for either classification (when responses are binary variables) or prediction (when responses are continuous variables). In this case neural networks can be used for classification of failure root causes where the responses are binary variables (lead fracture or no fracture, open circuit or no issue, etc.).

Each node of a hidden layer has an individual activation function (transfer function) that is chosen by the modeler and defines the relationship between the node in the hidden layer and the nodes in the input layer. The activation function can be different forms of transformation, including linear, hyperbolic tangent (Tan h), Gaussian radial basis function, and others. The activation function between the output node and nodes of the hidden layer is predefined as either a linear function for continuous output or a logistic function for binary output.

Each activation function contains multiple weights. A linear activation function is very similar to a linear regression function. The weights are set as random values initially and are modified in an iterative manner. The criteria to optimize the weights is to minimize the sum of square errors (least squares method). Prediction error is defined as the difference between the prediction value and the actual output value. The sum of squared errors is decreased by modifying weights in the next iteration, until eventually it is small enough.

These methods outline several practical methods of implementing this concept for detecting potential lead pathway issues and providing that information to neurostimulation system 100 for potential electrode pathway reconfiguration options as well as potentially informing the clinician or patient in the event that reconfiguration is unable to remedy the problem based upon the patient's ability to satisfactorily adjust their therapy.

In order to act upon a suspect lead path and continue to provide necessary therapy to the patient without clinical intervention, embodiments of neurostimulation system 100 can implement automatic electrode pathway reconfiguration. Selection of an alternative pathway can be based on previous measurements of known good electrode pathways as well as proximity to the previous programmed configuration, in order to achieve the same or a similar beneficial therapy for the patient. Typically, the direction of electrode configuration change would tend towards electrodes closer to the patient's head for pain stimulation therapy, though this is not true in all cases. A variety of locations could be utilized, even alternating between two or more configurations around a suspected compromised electrode.

Figure 17:
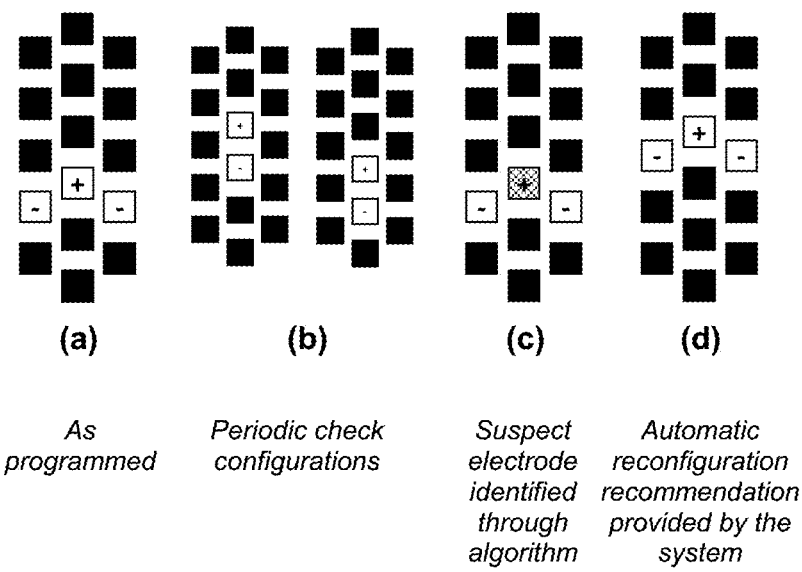
FIG. 17 depicts a programmed electrode configuration, a periodic check electrode configuration, an identified suspected electrode, and an automatically identified electrode reconfiguration according to an embodiment.
Figure 18:
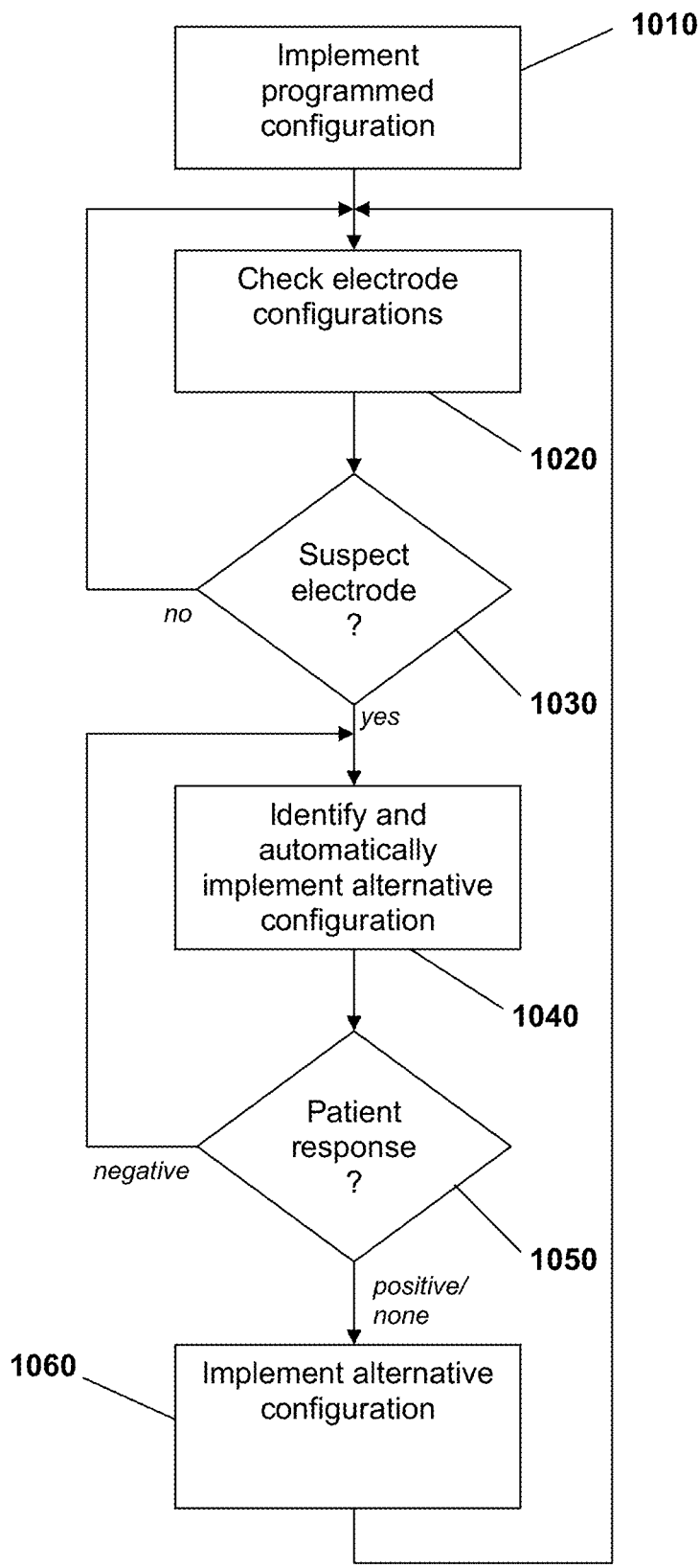
FIG. 18 depicts a flowchart of a method according to an embodiment.

An example of a potential reconfiguration is illustrated in FIG. 17, and a flowchart for a related method is depicted in FIG. 18. At (a) in FIG. 17, the programmed electrode configuration is shown. In FIG. 18, this configuration is implemented in operation of neurostimulation system 100 at 1010. According to the approach discussed above, periodic checks of the electrodes are conducted according to the pattern depicted at (b) in FIG. 17, at 1020 in FIG. 18. Based on the results of these checks and the other data and information informing the algorithm, a suspect electrode is identified, shown in cross-hatching in (c) in FIG. 17 and at 1030 in FIG. 18. Neurostimulation system 100 then can recommend and automatically implement an electrode reconfiguration in order to achieve the same or a suitably similar therapy for the patient, at 1040 in FIG. 18. This is shown in (d) in FIG. 17, where the electrodes immediately adjacent distally to the programmed set of electrodes are selected and then used to deliver stimulation therapy, avoiding the suspect electrode. As discussed above, this can be the next closest set of electrodes towards the head of the patient.

In some embodiments, the system can require confirmation or input, such as from a clinician, before implementing an electrode reconfiguration. In embodiments in which this is done automatically, however, it can provide advantages to the patient, such as a continuation of therapy (which may be perceived as the same as that delivered by the programmed electrodes) without the need to seek clinical intervention.

After an automatic reconfiguration, neurostimulation system 100 can monitor a potential patient response to see if amplitude stimulation adjustments are within the programmed limits, i.e., the patient is not trying to "max out" their allowed stimulation levels in order to obtain relief. This is shown at 1050 in FIG. 18. If such an observation is made, then the reconfiguration may not be optimal or suitable, and a new reconfiguration recommendation can be attempted. Absent such an observation, the alternative configuration can continue to be implemented, at 1060.

This methodology for timely and accurate lead integrity monitoring and automatic reconfiguration can be utilized to reduce complaints related to excessive lead impedance and instances of loss of therapy. The automatic nature of the detection and reconfiguration, when successful in providing an alternative therapy pathway without active clinician involvement, can improve the dependability of neurostimulation and neuromodulation systems and provide benefits for patients and the efficacy of the therapy for a variety of conditions. The sophistication of the algorithms can also minimize false-positive lead pathway integrity warnings that can lead to clinical intervention, user/patient dissatisfaction, and complaint generation.

While discussed in the context of implantable neurostimulation and neuromodulation systems, the algorithms, methodologies and approaches discussed herein can have applicability in other medical devices and systems.

Therefore, in one embodiment a system is configured to provide therapeutic electrical stimulation to target tissue and comprises a electrical stimulation generator configured to generate electrical stimulation pulses; one or more leads each comprising a plurality of electrodes, the one or more leads electrically coupled with the electrical stimulation generator to deliver the electrical stimulation pulses to the target tissue via the plurality of electrodes; and control circuitry comprising memory storing a stimulation program defining therapeutic electrical stimulation to be generated by the electrical stimulation generator and provided to the at least one of the plurality of electrodes, the control circuitry configured to control the electrical stimulation generator to generate the electrical stimulation pulses, measure over time impedances of a current pathway associated with at least one electrode of the plurality of electrodes, monitor at least one impedance trend associated with the current pathway, and determine, by applying a predictive model based on the at least one impedance trend and historical lead reliability data, whether the at least one impedance trend is related to a fault in the pathway or a physiological change.

The historical lead reliability data can include the probability of failure of a lead as a function of expected useful life of the lead.

The measuring can include applying at least one pulse between a pair of the plurality of electrodes.

The at least one impedance trend can comprise impedance data from multiple ones of the plurality of electrodes.

The predictive model can comprise at least one historical assumption of integrity over time of a lead and electrode pathway.

The at least one historical assumption of integrity over time of a lead and electrode pathway can comprise at least one of a beginning of lead life assumption, a useful lead life assumption, or an end of lead life assumption.

If the control circuitry determines that the at least one impedance trend is related to a fault in a particular electrode pathway, the control circuitry can be configured to automatically identify and modify the stimulation program defining a therapeutic electrical stimulation by replacing the particular electrode pathway with a first alternative pathway having at least one different electrode than the particular pathway.

The system also can comprise a programmer device communicatively coupled with the control circuitry, and the programmer device can be configured to receive patient input and to select and implement a second alternative pathway based on the patient input.

The programmer device can comprise at least a portion of the control circuitry.

The control circuitry can be remote from at least one of the programmer device or the electrical stimulation generator.

The electrical stimulation generator can be co-located with at least a portion of the control circuitry.

The predictive model can be further configured to determine, based on patient input, whether the at least one impedance trend is related to a fault in the programmed pathway or a physiological change.

The system can be an implantable neurostimulation system.

In another embodiment, a pathway integrity monitoring and reconfiguration system for electrical stimulation lead management can comprise a stimulation device including one or more leads and configured to provide therapeutic electrical stimulation to target tissue via a plurality of electrodes of the one or more leads; a lead integrity tester coupled to the one or more leads and configured to measure one or more electrical pathway integrity parameters of the one or more leads; a lead integrity memory module coupled to the lead integrity tester and configured to store at least the one or more electrical pathway integrity parameters for each occurrence of measurement of the one or more electrical pathway integrity parameters; and a controller coupled to the one or more leads and the lead integrity memory and configured to control the one or more leads based on a predictive model generated by analyzing the measurements of the one or more electrical pathway integrity parameters over a period of time.

In still another embodiment, a method of monitoring pathway integrity and automatically implementing pathway reconfiguration in a system can comprise delivering electrical stimulation via at least one pathway; measuring an impedance in the system related to delivering at least one pulse via the at least one pathway; storing, via circuitry of the system, the measured impedance for a plurality of pulses and identifying at least one trend in the stored measured impedances; storing historical data via the circuitry; storing instructions via the circuitry for a predictive model to utilize the at least one trend and the historical data; and generating, via the system, an output when application of the predictive model determines that the at least one trend is related to a fault in one or more of the at least one pathway.

The method can further comprise defining the pathway by an electrode on a lead of the system.

In the method, measuring an impedance in the system can further comprise measuring the impedance between a pair of electrodes on a lead.

In the method, measuring an impedance in the system can further comprise measuring impedances between multiple different pairs of electrodes on the lead.

The method can further comprise automatically identifying and implementing a first alternative pathway different from the at least one pathway if application of the predictive model determines that the at least one trend is related to a fault in the at least one pathway.

The method can further comprise receiving, via a programmer device, patient input in response to the implementation of the first alternative pathway.

The method can further comprise selecting and implementing a second alternative pathway based on the received patient input.

In the method, the historical data can include historical lead reliability data of a probability of failure of a lead as a function of expected useful life of the lead.

In the method, the predictive model can comprise at least one historical assumption of integrity over time of a lead and electrode pathway.

In the method, the at least one historical assumption of integrity over time of a lead and electrode pathway can comprise at least one of a beginning of lead life assumption, a useful lead life assumption, or an end of lead life assumption.

If the predictive model determines that the at least one impedance trend is related to a fault in a particular electrode pathway, the method further comprises automatically identifying and modifying the electrical stimulation by replacing the at least one pathway with a first alternative pathway having at least one different electrode than the at least one pathway.

Features and components of different embodiments discussed herein can be combined in other embodiments. In this way particular illumination effects can be designed and achieved in order to meet particular desires or needs in the industry.

Various embodiments of systems, devices, and methods have been described herein. These embodiments are given only by way of example and are not intended to limit the scope of the claimed inventions. It should be appreciated, moreover, that the various features of the embodiments that have been described may be combined in various ways to produce numerous additional embodiments. Moreover, while various materials, dimensions, shapes, configurations and locations, etc. have been described for use with disclosed embodiments, others besides those disclosed may be utilized without exceeding the scope of the claimed inventions.

Persons of ordinary skill in the relevant arts will recognize that the subject matter hereof may comprise fewer features than illustrated in any individual embodiment described above. The embodiments described herein are not meant to be an exhaustive presentation of the ways in which the various features of the subject matter hereof may be combined. Accordingly, the embodiments are not mutually exclusive combinations of features; rather, the various embodiments can comprise a combination of different individual features selected from different individual embodiments, as understood by persons of ordinary skill in the art. Moreover, elements described with respect to one embodiment can be implemented in other embodiments even when not described in such embodiments unless otherwise noted.

Although a dependent claim may refer in the claims to a specific combination with one or more other claims, other embodiments can also include a combination of the dependent claim with the subject matter of each other dependent claim or a combination of one or more features with other dependent or independent claims. Such combinations are proposed herein unless it is stated that a specific combination is not intended.

Any incorporation by reference of documents above is limited such that no subject matter is incorporated that is contrary to the explicit disclosure herein. Any incorporation by reference of documents above is further limited such that no claims included in the documents are incorporated by reference herein. Any incorporation by reference of documents above is yet further limited such that any definitions provided in the documents are not incorporated by reference herein unless expressly included herein.

For purposes of interpreting the claims, it is expressly intended that the provisions of 35 U.S.C. § 112(f) are not to be invoked unless the specific terms "means for" or "step for" are recited in a claim.

The invention claimed is:

1. A system configured to provide therapeutic electrical stimulation to target tissue and comprising:
   a electrical stimulation generator configured to generate electrical stimulation pulses;

one or more leads each comprising a plurality of electrodes, the one or more leads electrically coupled with the electrical stimulation generator to deliver the electrical stimulation pulses to the target tissue via the plurality of electrodes; and control circuitry comprising memory storing a stimulation program defining therapeutic electrical stimulation to be generated by the electrical stimulation generator and provided to the at least one of the plurality of electrodes, the control circuitry configured to:

control the electrical stimulation generator to generate the electrical stimulation pulses, measure and over time collect impedances of a current pathway as well as a plurality of alternate pathways associated with the plurality of electrodes by applying a series of test pulses to each pathway, monitor an impedance trend associated with the current pathway and the plurality of alternate pathways, and determine, by applying a predictive model based on the impedance trends of the current pathway and the plurality of alternate pathways and historical lead reliability data, whether a perceived change in the impedance trend of the current pathway is related to a fault in the pathway or a physiological change.

2. The system of claim 1, wherein the historical lead reliability data includes the probability of failure of a lead as a function of expected useful life of the lead.

3. The system of claim 1, wherein the measuring includes applying at least one pulse between a pair of the plurality of electrodes.

4. The system of claim 1, wherein the at least one impedance trend comprises impedance data from multiple ones of the plurality of electrodes.

5. The system of claim 1, wherein the predictive model comprises at least one historical assumption of integrity over time of a lead and electrode pathway.

6. The system of claim 5, wherein the at least one historical assumption of integrity over time of a lead and electrode pathway comprises at least one of a beginning of lead life assumption, a useful lead life assumption, or an end of lead life assumption.

7. The system of claim 1, wherein, if the control circuitry determines that the at least one impedance trend is related to a fault in a particular electrode pathway, the control circuitry is configured to automatically identify and modify the stimulation program defining a therapeutic electrical stimulation by replacing the particular electrode pathway with a first alternative pathway having at least one different electrode than the particular pathway.

8. The system of claim 7, further comprising a programmer device communicatively coupled with the control circuitry, wherein the programmer device is configured to receive patient input, and wherein the control circuitry is configured to select and implement a second alternative pathway based on the patient input.

9. The system of claim 8, wherein the programmer device comprises at least a portion of the control circuitry.

10. The system of claim 8, wherein the control circuitry is remote from at least one of the programmer device or the electrical stimulation generator.

11. The system of claim 1, wherein the electrical stimulation generator is co-located with at least a portion of the control circuitry.

12. The system of claim 1, wherein the predictive model also is configured to determine, based on patient input, whether the at least one impedance trend is related to a fault in the programmed pathway or a physiological change.

13. The system of claim 1, wherein the system is an implantable neurostimulation system.

14. A pathway integrity monitoring and reconfiguration system for electrical stimulation lead management, comprising:

a stimulation device including one or more leads and configured to provide therapeutic electrical stimulation to target tissue via a plurality of electrodes of the one or more leads;

a lead integrity tester coupled to the one or more leads and configured to measure one or more electrical pathway integrity parameters of a current pathway and a plurality of alternate pathways associated with the plurality of electrodes by applying a series of test pulses to each pathway;

a lead integrity memory module coupled to the lead integrity tester and configured to store at least the one or more electrical pathway integrity parameters for each occurrence of measurement of the one or more electrical pathway integrity parameters; and a controller coupled to the one or more leads and the lead integrity memory module and configured to select one of the plurality of alternate pathways for stimulation based on a predictive model generated by analyzing historical lead reliability data along with trends in the measurements of the one or more electrical pathway integrity parameters of the current pathway in a plurality of alternate pathways over a period of time.

15. A method of monitoring pathway integrity and automatically implementing pathway reconfiguration in a system comprising:

delivering electrical stimulation via at least one pathway;

measuring an impedance in the system related to delivering at least one pulse via the at least one pathway and a plurality of alternate pathways;

storing, via circuitry of the system, the measured impedance for a plurality of pulses and identifying a corresponding plurality of trends in the stored measured impedances;

storing observed patient responses and historical data via the circuitry;

storing instructions via the circuitry for a predictive model to utilize a combination of the observed patient responses, the plurality of trends in the measured impedances of the at least one pathway and the plurality of alternate pathways, and the historical data to determine whether change in a trend of the at least one pathway is related to a fault in the pathway or a physiological change; and generating, via the system, an output when application of the predictive model determines that the at least one trend is related to a fault in one or more of the at least one pathway.

16. The method of claim 15, further comprising defining the pathway by an electrode on a lead of the system.

17. The method of claim 16, wherein measuring an impedance in the system further comprises measuring the impedance between a pair of electrodes on a lead.

18. The method of claim 17, wherein measuring an impedance in the system further comprises measuring impedances between multiple different pairs of electrodes on the lead.

19. The method of claim 15, further comprising automatically identifying and implementing a first alternative pathway different from the at least one pathway if application of the predictive model determines that the at least one trend is related to a fault in the at least one pathway.

20. The method of claim 19, further comprising receiving, via a programmer device, patient input in response to the implementation of the first alternative pathway.

21. The method of claim 20, further comprising selecting and implementing a second alternative pathway based on the received patient input.

22. The method of claim 15, wherein the historical data includes historical lead reliability data of a probability of failure of a lead as a function of expected useful life of the lead.

23. The method of claim 15, wherein the predictive model comprises at least one historical assumption of integrity over time of a lead and electrode pathway.

24. The method of claim 23, wherein the at least one historical assumption of integrity over time of a lead and electrode pathway comprises at least one of a beginning of lead life assumption, a useful lead life assumption, or an end of lead life assumption.

25. The method of claim 15, wherein, if the predictive model determines that the at least one impedance trend is related to a fault in a particular electrode pathway, the method further comprises automatically identifying and modifying the electrical stimulation by replacing the at least one pathway with a first alternative pathway having at least one different electrode than the at least one pathway.

* * * * *